United States Patent [19]

Pedrazzini

[11] Patent Number: 4,474,499
[45] Date of Patent: Oct. 2, 1984

[54] PROCESS FOR CONSTRUCTING AN ATTACHMENT CONNECTION FOR A DENTAL PROSTHESIS

[76] Inventor: Francesco Pedrazzini, Cramer Klett Str. 16b, 8014 Neubiberg, Fed. Rep. of Germany

[21] Appl. No.: 456,094

[22] Filed: Jan. 6, 1983

[30] Foreign Application Priority Data

Jan. 19, 1982 [DE] Fed. Rep. of Germany ....... 3201391

[51] Int. Cl.³ ............................................. A61C 13/22
[52] U.S. Cl. .................................... 433/181; 433/177; 433/182; 433/213
[58] Field of Search ............... 433/181, 182, 183, 172, 433/177, 178, 213

[56] References Cited

U.S. PATENT DOCUMENTS

| | | | |
|---|---|---|---|
| 1,702,282 | 2/1929 | Stoloff | 433/172 |
| 3,117,377 | 1/1964 | Poveromo | 433/182 |
| 3,344,842 | 10/1967 | Cameron | 433/181 |
| 3,613,244 | 10/1971 | Flecher | 433/172 |
| 3,710,446 | 1/1973 | Poveromo | 433/182 |
| 4,196,516 | 4/1980 | Poveromo | 433/182 |
| 4,348,181 | 9/1982 | Dawson | 433/172 |

FOREIGN PATENT DOCUMENTS 556843 5/1958 Canada ................................. 433/172
1928150 4/1979 Fed. Rep. of Germany ...... 433/172

Primary Examiner—John J. Wilson
Attorney, Agent, or Firm—Orrin M. Haugen; Thomas J. Nikolai; Douglas L. Tschida

[57] ABSTRACT

An attachment connection between a dental prosthesis body and/or a dental bridge and an anchoring tooth and/or a crown consists of a female die hollow space (5) provided in an anchoring tooth and/or the crown, for acceptance of a male die (7) which, with its anchoring part (9), is capable of being introduced into a housing (23) for attachment of the male die (7). In order to simplify the precision of fit of the attachment connection and the construction process for this attachment connection, the housing (23), which is arranged on a dental prosthesis body and/or a dental bridge, is structured in one piece with this dental prosthesis body and/or the dental bridge by means of a bonding substance with the housing (23) surrounding the anchoring part (9) of the male die (7) in box-fashion. Used in the construction of the housing (23) on the dental prosthesis body and/or a dental bridge is a prefabricated secondary male die (15) with a housing shaper (17), advantageously made of ceramic, the form of which corresponds to the shape of the male die (7) with its anchoring part (9) (FIG. 7).

7 Claims, 21 Drawing Figures

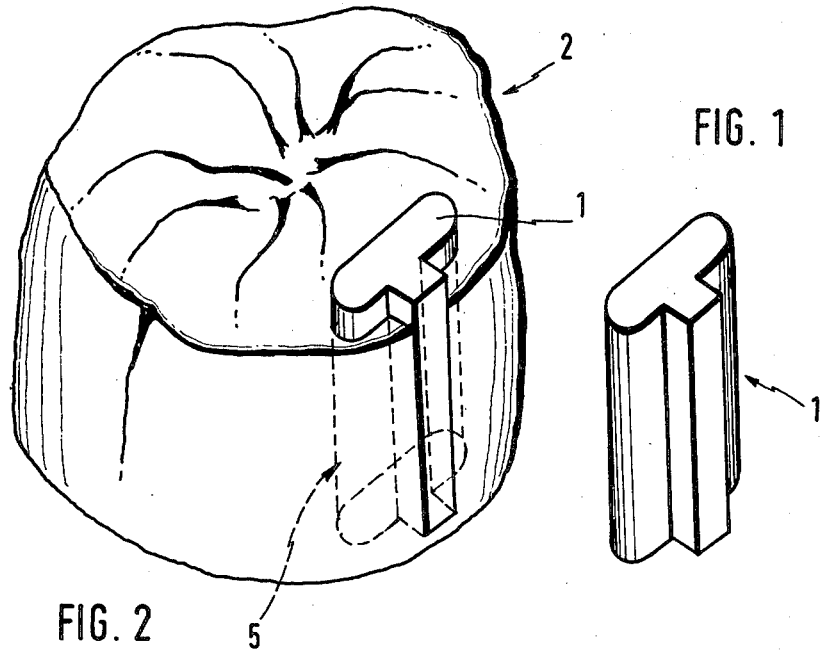
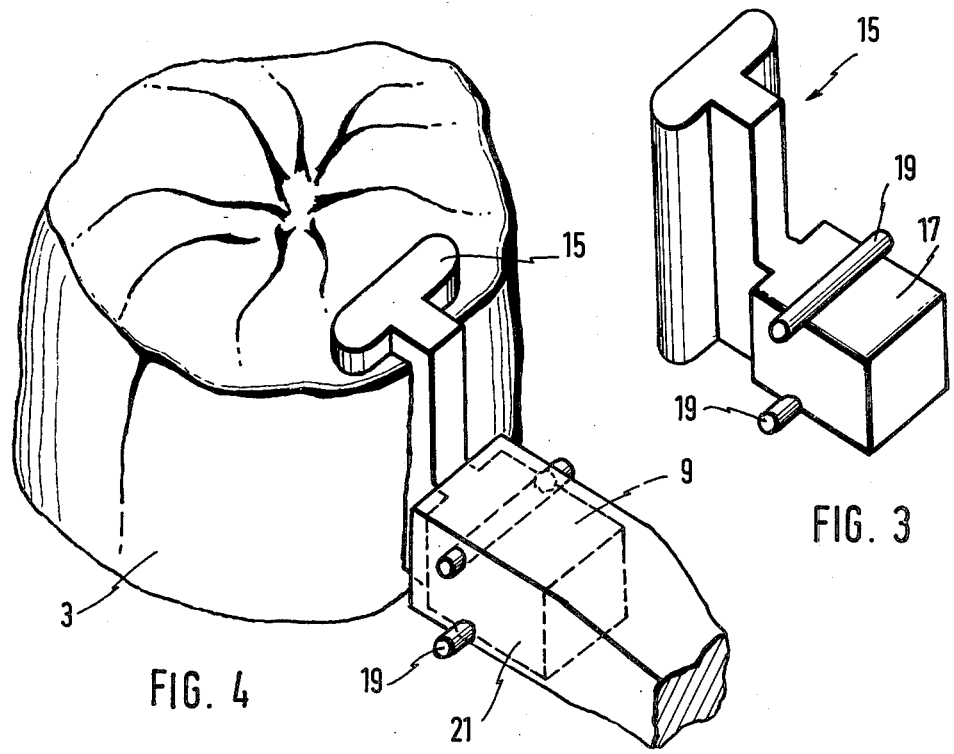

FIG. 9a
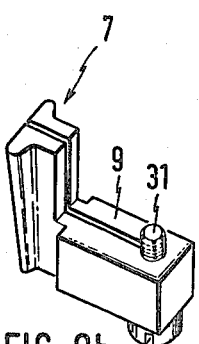
FIG. 9b  FIG. 9c
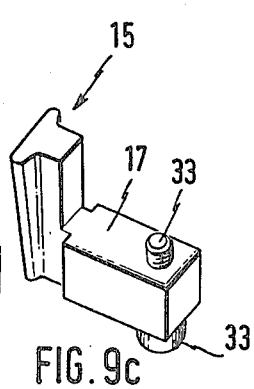
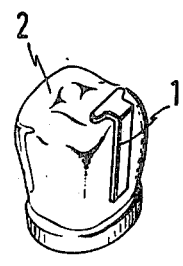
FIG. 10a
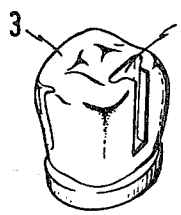
FIG. 10b
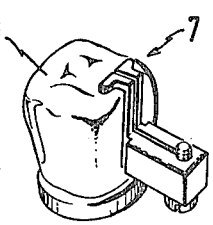
FIG. 10c
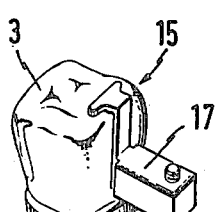
FIG. 10d
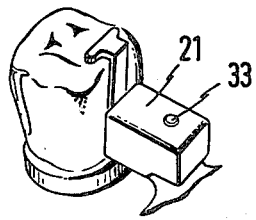
FIG. 10e
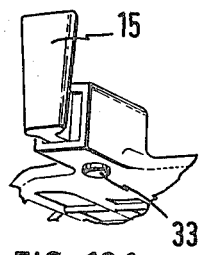
FIG. 10f  FIG. 10g
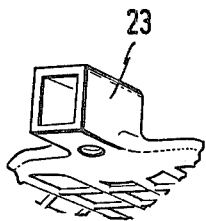
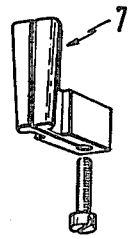
FIG. 10h
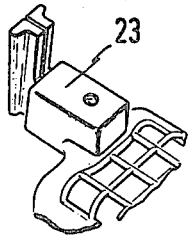
FIG. 10i
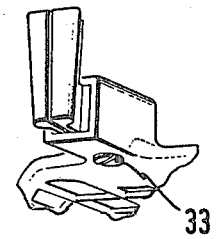
FIG. 10j

PROCESS FOR CONSTRUCTING AN ATTACHMENT CONNECTION FOR A DENTAL PROSTHESIS

BACKGROUND OF THE INVENTION

This invention relates generally to a method and apparatus for establishing an attachment connection between a dental prosthesis body such as a dental bridge and an anchoring tooth or crown, and more specifically to a construction of a precision attachment connection which is relatively simple to produce, and effective in its use.

In dentistry, attachments have a great importance, in particular, in the case of a partial plate or bridge or any other removable dental prosthesis. In these cases, the female die of the attachment mechanically joins, via the male die of the attachment, a prosthesis body with a crown or with an anchoring tooth. Attachment fittings of the prior art are essentially a concentric double anchoring system. They consist of a fitting part, namely a female die with a hollow or negative form, and a male die as a positive form. In general, the female die is provided on a crown or on an anchoring tooth, while the male die is anchored to the prosthesis part. There are principally two basic types of connections between a dental prosthesis body and an anchoring tooth. In one type, a male die is cast on the dental prosthesis body. In this arrangement, however, numerous problems occur principally due to the difficulty in accuracy in the dimensions of the parts comprising the entire arrangement. Unless accurately formed, the attachment can be fitted together only with difficulty and the parts of the attachment can be separated from one another only with difficulty.

The second type of connection involves producing, on a crown and/or on an anchoring tooth, a corresponding recess for acceptance of a female die body. The female die body, in this case, is welded into this anchoring tooth. Then, likewise welded on the prosthesis part that is to be joined with the anchoring tooth is a housing for attachment of a male die body. Additionally, the male die body is provided with an anchoring part that can be fitted into the housing in question and locked in place. Here, the housing is welded to a so-called skeleton prosthesis, and an appropriate flesh-colored plastic, protective coating is placed over this skeleton prosthesis and the housing.

When anchoring a dental prosthesis, for example a replacement for the lower back teeth, to a front dental crown, four extremely expensive welding procedures are needed for joining the corresponding female die and housing bodies which are used to accept the male die. These welding steps are often found to introduce alignment problems. Since the corresponding welding of the housing parts and of the female die body must be done with adequate precision in order to be able to introduce the male die into the female die body easily and without canting, this procedure has not been too satisfactory.

Moreover, there is always a further disadvantage, in particular when using the so-called "burn-on" technique. The use of this technique, in particular for front tooth parts, involves burning onto a noble metal alloy, at high temperatures (over 1000° C.) tooth front parts consisting of natural tooth-like ceramic. It is found that when burning on the ceramic at such temperatures, the corresponding weld spots run out. As such, there is the danger that the corresponding female die bodies will break off with strong stresses.

Dental casting techniques are also known with respect to the mounting of an attachment part on a skeleton prosthesis. Here, a housing for the anchoring part of a male die is formed which is capable of being firmly screwed on. This process affords the advantage that the male die, which may consist of V2H steel, is interchangeable. Accordingly, firm screwing down of the housing to an attachment part requires an additional work step wherein a firm and stable connection becomes possible only in a limited number of cases.

SUMMARY OF THE INVENTION

The present invention is intended to improve the attachment connection between a dental prosthesis body and/or a dental bridge and an anchoring tooth and/or a crown through the use of an interchangeable male die that is capable of being attached inside of a housing. It includes both a method and an apparatus for constructing an attachment connection whereby the precision of fit is increased. In carrying out the invention, prior to the production of a cast model, the dental prosthesis body is produced in common with a wax housing through the use of a prefabricated housing shaper whose configuration corresponds to the anchoring portion of the male die. More specifically, a secondary male die is fitted into the female die hollow space in the anchoring tooth at the time that the wax housing defining the anchoring part is molded. As such, there is a precise fit and alignment between the anchoring portion of the male die and the housing portion and interconnecting crib of the prosthesis which is to be ultimately joined to the male die.

This invention provides for the first time, in optimal fashion, a stable attachment connection between a dental prosthesis body and an anchoring tooth which utilizes simple procedures, yet affords a precision fit.

Above all, however, even when the method and apparatus of the present invention are used in conjunction with the so-called burn-on technique of fastening ceramic tooth components to gold or platinum alloy, the problem of a welded spot giving way is avoided. Furthermore, the present invention is advantageous when joining the male die and the female die form to an anchoring tooth or to a crown, in that the problem of canting of the two parts is reduced. Proper alignment is made possible by the fact that a common wax model of the housing and of the dental prosthesis body and/or the dental bridge is produced through the use of a prefabricated housing form corresponding to the anchoring part of the male die. Molding of the wax housing is accomplished through the use of a secondary male die which includes both the housing shaper and a male die corresponding with the anchoring part, whereby the secondary male die can be pushed into the female die hollow space formed in the anchoring tooth and/or the crown. The secondary male die may consist of the same ceramic material as the female die shaper that is used for constructing the corresponding hollow space or recess in the anchoring tooth.

In this fashion, the fit and size tolerances are maintained due to the fact that when forming the recess in the anchoring tooth and when forming the housing, a wax impression is first made into the form of the anchoring tooth and incorporating a hollow cylinder which is appropriately filled with an embedding mass. Since, upon heating the entire arrangement, wax flows out through appropriately provided casting channels, it is possible to pour into the hollow space remaining in the embedded mass an appropriate alloy for production of the dental prosthesis part and/or the anchoring tooth. Since the same heat resistant material is used for constructing the female die shaper as is used for the secondary male die part used in the formation of the housing, it is possible to achieve the same results for both parts, as far as size precision is concerned. That is, precision of fit of the male die, made of noble metal or preferably of V2H steel, both within the hollow space formed in the anchoring tooth and within the confines of the housing portion of the dental prosthesis is obtained.

It is to be noted that the wax housing completely encloses the housing shaper portion of the secondary male die which defines the anchoring part of the final male die on all sides except the side facing the secondary male die. As such, an optimal and firm hold is later guaranteed between mating parts.

Further advantages, particulars and features of the invention are obtained in the following from the description of the invention based on the drawings.

DESCRIPTION OF THE DRAWINGS

FIG. 1: A female die shaper;

FIG. 2: The model of a wax crown incorporating a female die shaper;

FIG. 3: A secondary male die part used in the molding of a housing for receiving an anchoring part of a male die;

FIG. 4: A solid cast crown poured in accordance with the wax model of FIG. 2, with the secondary part of FIG. 3 set in for molding the housing for acceptance of a male die;

FIG. 9a: An alternate embodiment having a slightly conically running female die shaper;

FIG. 9b: A male die corresponding to this alternative embodiment;

FIG. 9c: A housing shaper made of ceramic; and

FIG. 10 to 10j: illustration of the different sequential work steps used in carrying out the method of the present invention.

DESCRIPTION OF THE PREFERRED EMBODIMENT

Figures 5, 6:
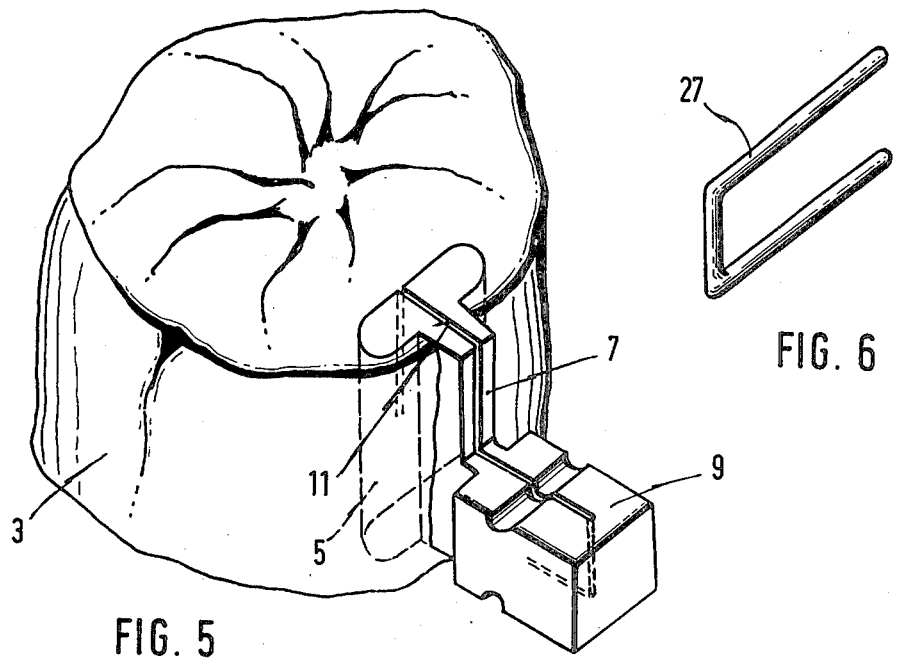
FIG. 5: The solid cast crown incorporating the male die and particulary illustrating the anchoring part.
FIG. 6: A U-shaped locking member for connection of the anchoring part of the male die within the housing.

Explained in the following will be the production and construction of a connection, by means of a male die and a housing, between a wax crown and a dental prosthesis.

In FIG. 1, identified by numeral 1, is a male die which in the following description will be referred to as a female die shaper. The female die shaper 1 has an essentially oval cross section. In FIG. 2, this female die shaper 1 is shown as being molded into a corresponding wax crown 2 to form an appropriate hollow space 5 for acceptance of a male die 15. The female die shaper 1 preferably consists of heat resistant ceramic and is held and directed by means of a suitable fixture (not shown) during molding.

The thus molded wax crown 2 formed into a muffle including a hollow cylinder generated by the female die shaper 1. Next, the entire inner hollow space of the muffle is filled with a suitable embedding mass. After the embedding mass has hardened, the muffle is heated in an oven, for example at 800° C., whereby the wax melts and flows downwardly via casting channels. However, the female die shaper 1 being constructed of a heat resistant ceramic, it remains in place in the embedding mass. In this fashion, after the wax flows out, there remains impressed in the embedding mass a hollow space corresponding to the dental crown that is to be molded. By way of further example, using the known centrifugal casting process, an alloy or even a noble metal such as gold may be injected through the casting channels into the hollow space left by the wax after it has flowed out, whereby a molded dental crown is created.

The female die shaper 1 that remains behind in the thinly structured solid cast crown 3 (FIG. 4), the form of which corresponds to the molded wax crown 2, is then removed by either a sand blasting technique or disengaged by means of an etching acid. Remaining behind in the solid cast crown 3 is a hollow space 5 having the shape of the female die.

Next, and with reference to FIG. 5, a male die member 7 having an anchoring part 9 is set into the hollow space 5 of the solid cast crown 3 and processed. That is, the male die 7 is shortened, ground down and its surface is shaped to blend in with the chewing surfaces of the solid cast crown 3. The male die 7 is a precision part that must be fitted quite precisely to the hollow space 5. Additionally, provided along the axis of symmetry of the male die member 7 is an actuating slot 11 that terminates in the anchoring part 9. Because of this longitudinal cut in the male die, it can be compressed easily and inserted into the hollow space 5 without canting.

After the male die 7 has its surfaces suitably shaped based on this fitting procedure, it is again removed from the hollow space 5 of the solid cast crown 3. As is to be seen in particular from FIG. 3 and FIG. 4, the secondary male die member 15 is next inserted into the hollow space 5 of the solid cast crown 3.

Here, the secondary male die 15 likewise consists of heat resistant ceramic and displays a shape corresponding to the female die shaper 1. In addition, however, the secondary male die includes a housing shaper 17 that corresponds to the anchoring part 9 of the final male die 7 (FIG. 5). Additionally, provided on the housing shaper 17 are tubular members 19, the importance of which will be explained in greater detail below. As can be further seen from FIGS. 3 and 5, the anchoring part 9 of the male die 7 extends normally to the male die 7 proximate its lower end. The anchoring part 9, as illustrated, has a polygonal cross section, i.e., a square or rectangular cross section. The same shape is given to the housing shaper 17 of the secondary male die 15.

As can best be seen from FIG. 4, molded about the housing shaper 17 is a wax housing 21 configured to generate a housing for accepting the anchoring part 9 of the male die 7. Although not shown in more detail, the wax housing 21 is molded from wax in common with a skeleton prosthesis. Here, the wax molding is constructed such that it completely surrounds the housing shaper 17 on five sides with the side that is facing the secondary male die 15 being exposed. This arrangement subsequently enables an optimum, stable and solid seating of the male die 7 within a housing 23.

This wax model of the housing 21 with the prosthesis and/or bridge molded on is placed into a muffle along with the secondary male die 15 and heated in an oven. In doing this, the wax flows out, leaving the male die 15, consisting of heat resistant ceramic disposed in the embedding mass. A suitable metal alloy is then poured into the hollow space created by the flow of the melted wax such that a one-piece structure with the housing 23 joined to the prosthesis results. The portion 17 of the secondary ceramic male die 15 that is still inside housing 23 is likewise blown out by means of a sand blasting apparatus or disengaged with acid. The tubular members 19 were also embedded as a part of the secondary die and because these tubular members have a greater width than the width of the anchoring part 9, and are contained in the cast housing 23, they must also be blown out by means of the sand blaster and/or disengaged by means of the acid. In doing so, two openings 25 are created on both sides of the housing 9.

Next, the processed male die 7 with its anchoring part 9 is pushed into the precisely fitting housing 23, which is integral with the prosthesis (not shown). By means of a U-shaped bracket 27, the male die 7 can be firmly locked in the housing 23 by means of a U-shaped clip 27 which is arranged to be pushed into the housing 23 through the openings 25. The legs of the clip 27 fit into semicircular recesses formed on the upper and lower side of the anchoring part 9 of the male die 7 as well as in corresponding semicircular shaped recesses on the inner side of housing 23, which were formed by the tubular members 19 during the casting of the housing 23.

Figure 7:
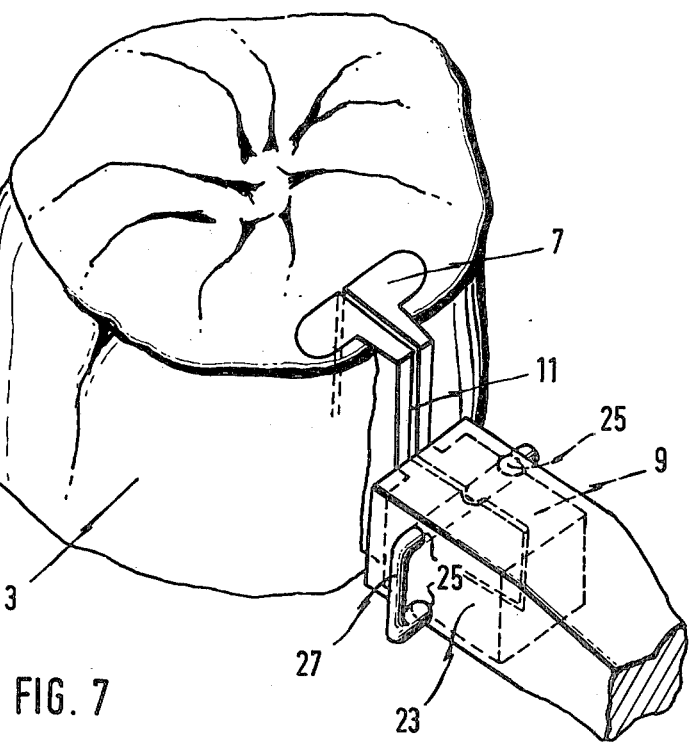
FIG. 7: The solid cast crown, which is firmly connected with a prosthesis via the male die and the housing.

The male die 7, one securely anchored to the housing and to the prosthesis (not shown) is introduced, together with the prosthesis, into the female die shaped hollow space 5 of the solid cast crown 3, whereby a secure attachment connection is produced (FIG. 7).

Figure 8:
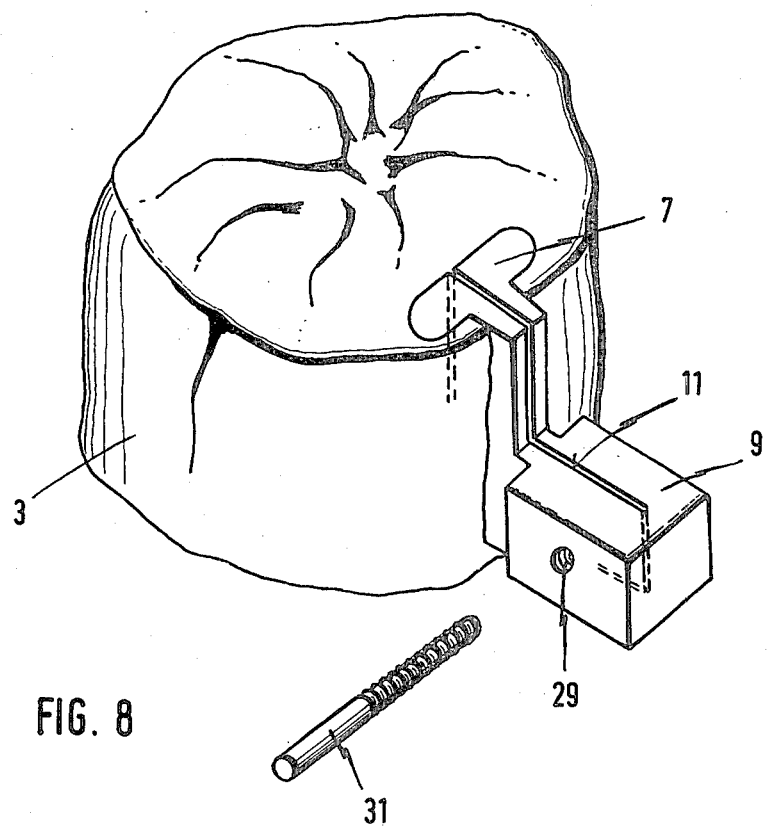
FIG. 8: Another form of embodiment of the male die with corresponding anchoring part.

It is to be understood that alternative means, other than a U-shaped clip 27, can be employed to anchor the male die 7 in the housing. For example, a bar, a pin or like device can be used. In this regard, FIG. 8 shows a male die 7 with an internally threaded bore 29. If a corresponding opening is provided in housing 23 when pouring, it is then possible to insert through this hole a screw 31 which extends into anchoring part 9 for locking the male die 7 to the housing 23. Alternatively, it is possible to screw in the screw from the bottom into the housing and into the anchoring part rather than from the side.

The invention will next be explained further in brief, summary fashion with the aid of a second exemplary embodiment. Shown in FIG. 9a is a female die shaper 1 with a form that tapers slightly conically downwardly. FIG. 9b shows the male die 7 with the anchoring part 9 and a screw 31 that can be rotated up from below. Shown in FIG. 9c is the secondary male die 15 with a housing shaper 17 having a shape corresponding to that of the anchoring part 9. The female die shaper 1 is preferably formed from ceramic. Provided on the housing shaper 17 are projections 33 corresponding in form to the screw 31, so that when the wax housing model is created, corresponding recesses are formed through which the screw 31 can be inserted for attaching the anchoring part 9 within the housing 17.

The individual work steps will be explained briefly in the following with the aid of FIGS. 10a to 10j:

FIG. 10a: First, a wax crown 2 with molded-in female die shaper 1 is constructed;

FIG. 10b: A solid crown 3 with corresponding female die hollow space 5 is constructed from the wax crown;

FIG. 10c: Next, the male die 7 is pushed into the female die hollow space 5, tested and finished so its surface conforms to the chewing surface of the tooth;

FIG. 10d: Next, the secondary male die 15 with its housing shaper 17 is set into the solid cast crown 3;

FIG. 10e: Placed about the female die shaper 1 is a molded wax housing 21 having the projections 33 on the housing shaper 17 extending up from below and through the wax housing 21 for forming a location for the screw 31;

FIG. 10f: Shows the finished wax molding in a front view with the secondary male die 15 and the lower projection 33;

FIG. 10g: As in the above-described manner, produced from the wax molding is a final cast model comprising the dental prosthesis (not shown) the interconnecting net-like crib and the housing 23;

FIG. 10h: Shows the male die 7 with withdrawn locking screw 31;

FIG. 10i: Shows housing 23 that is attached in one piece via the net-like crib to the dental prosthesis (not shown) with male die 7 inserted into the housing 23, prior to the insertion of the screw 31; and FIG. 10j: The male die 7 is firmly anchored to housing 23 via screw 31 that is rotated in from below.

In the exemplary embodiments shown, the male die 7 is illustrated as having an oval cross-section. However, it should be understood that the invention can likewise be used with attachments having a different geometry as, for example, a rectangular attachment wherein the oval cylinder is replaced by a fitting having a rectangular cross-section. Similarly, in the case of a T-attachment or a double T-attachment, a correspondingly structured male die may be designed. A trapeziodal attachement with a trapezoidal fitting, or a triangular attachment with a correspondingly shaped fitting for the male die may also be utilized. Also the configuration of the crib may vary depending upon the prosthesis to which it is attached.

The invention has been described herein in considerable detail in order to comply with the Patent Statutes and to provide those skilled in the art with the information needed to apply the novel principles, and to construct and use such specialized complements as are required. However, it is to be understood that the invention can be carried by specifically different equipment and devices, and that various modifications, both as to equipment details and operating procedures can be accomplished without departing from the scope of the invention itself.

What is claimed is:

1. A method for constructing a precision attachment connenction between a dental prosthesis body and an anchoring crown, comprising the steps of:

(a) forming a wax crown for an anchoring tooth, said wax crown containing a heat resistant female die member of a predetermined shape corresponding to that of a male portion of said attachment connection;

(b) constructing a solid crown from said wax crown containing said heat resistant female die, said solid crown having a hollow space corresponding in shape to said heat resistant female die member;

(c) forming a temporary heat resistant fixture having a housing shaper portion conforming in shape to an anchoring portion of said attachment connection and joined to a secondary male die member adapted to fit within said hollow space in said solid crown;

(d) forming a molded wax model of said dental prosthesis body, said model including a crib portion and a molded wax housing substantially enveloping said housing shaper portion;

(e) constructing a solid cast dental prosthesis having a housing portion and an integral crib portion from said molded wax model of said prosthesis; and (f) joining said solid crown to said solid cast dental prosthesis via an attachment device comprising a male die member resiliently compressible along an actuating slit and mountable within said hollow space and including an integrally formed anchoring portion mountable within the housing portion of said solid cast dental prosthesis.

2. The method as in claim 1 and further including the step of coupling said attachment device to said solid crown by inserting said male die member within said hollow space and conforming it to the chewing surfaces of said crown before forming said molded wax model of said dental prosthesis.

3. The method as in claim 2 wherein said secondary male die member and said housing shaper portion of said temporary fixture are formed from the same material as said female die member.

4. The method as in claim 1 wherein said temporary fixture is formed from ceramic.

5. The method as in claim 1 wherein said molded wax housing is configured to surround said housing shaper on all sides, except that facing said male die member.

6. The method as in claim 1 and further including the step of forming projections on said housing shaper for creating a corresponding recess in said molded wax housing of said molded wax model.

7. The method as in claim 6 wherein said joining step includes inserting a locking member into the corresponding recess formed in said solid cast dental prosthesis.

* * * * *